United States Patent [19]
Benjamin et al.

[11] 4,103,424
[45] Aug. 1, 1978

[54] DENTAL ARTICULATION APPARATUS AND METHOD

[75] Inventors: Adrian Benjamin; Walter G. Churgin, both of Millburn; Frederick Biermann, Maplewood; David W. Benjamin, Millington, all of N.J.; Finton P. Cordell, Lutherville, Md.; Robert M. Tempkin, Rochester; Carl A. Zambrano, New York, both of N.Y.; Peter Halasz, West Los Angeles, Calif.

[73] Assignee: Bergen Brunswig Corporation, Los Angeles, Calif.

[21] Appl. No.: 704,124

[22] Filed: Jul. 12, 1976

[51] Int. Cl.² ........................................... A61C 13/22
[52] U.S. Cl. ....................................................... 32/32
[58] Field of Search ............................................. 32/32

[56] References Cited

U.S. PATENT DOCUMENTS

| | | | |
|---|---|---|---|
| 1,614,828 | 1/1927 | Coffin | 32/32 |
| 2,270,561 | 1/1942 | Sanborn | 32/32 |
| 2,697,279 | 12/1954 | Clawson | 32/32 |
| 2,700,219 | 1/1955 | Lindley | 32/32 |
| 3,043,009 | 7/1962 | Whitman | 32/32 |
| 3,576,075 | 4/1971 | Scott | 32/32 |
| 3,823,476 | 7/1974 | Hudson | 32/32 |
| 3,882,602 | 5/1975 | Polanco | 32/32 |
| 3,930,312 | 1/1976 | Daub | 32/32 |
| 3,938,252 | 2/1976 | Polanco | 32/32 |

Primary Examiner—Robert Peshock
Attorney, Agent, or Firm—Romney, Schaap, Golant, Scillieri, Disner & Ashen

[57] ABSTRACT

A three element disposable apparatus for dental cast articulation made of plastic or the like comprising a pair of pivotally attached cup members having grid means for removably mounting plaster casts thereon. A vertical guide pin is lockable in the upper cup member to determine its front displacement from the lower cup member.

The inexpensive construction of this articulator makes it possible for each patient case to have its own new articulator.

3 Claims, 6 Drawing Figures

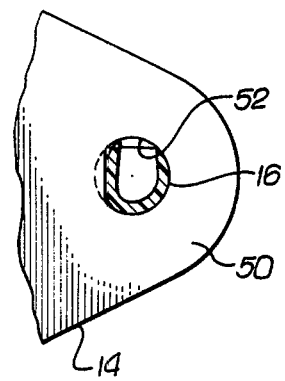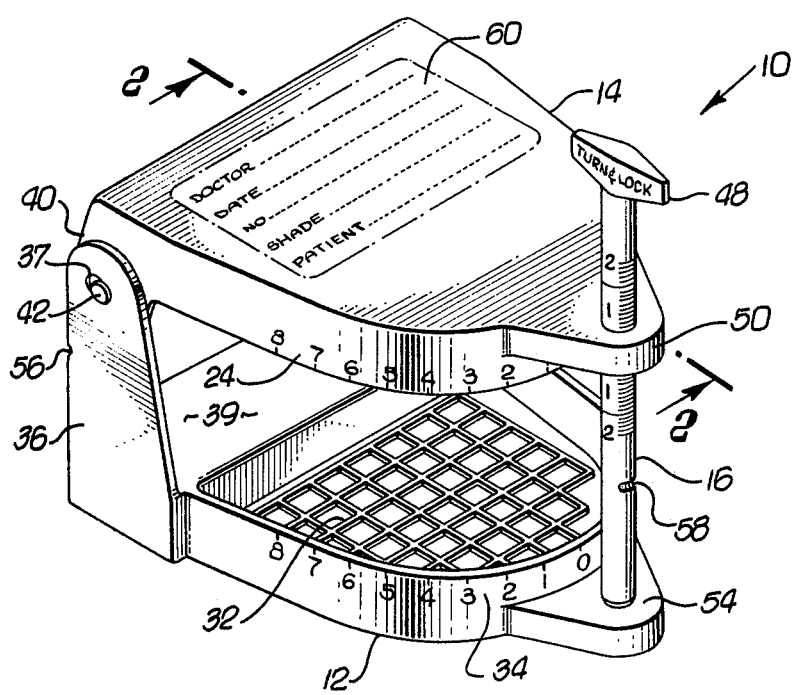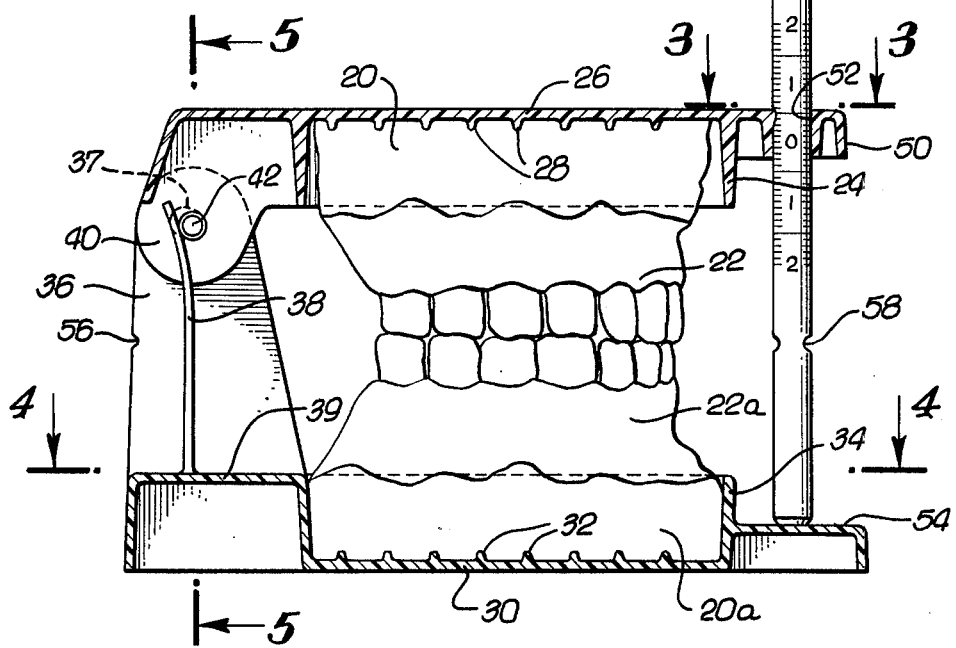

DENTAL ARTICULATION APPARATUS AND METHOD

BACKGROUND OF THE INVENTION

1. Field of the Invention

The present invention relates to dental articulators generally; more particularly, to an improved three element plastic articulator which removably mounts and remounts plaster casts and models on grid means located within top and bottom cup members.

2. Description of the Prior Art

The majority of dental articulators in use today are made of metal. Such metal articulators are relatively expensive. While less expensive plastic articulators are available, they are usually copied from their metal counterparts and lack the required rigidity, stability and precision necessary to successfully mount and/or remount dental casts or models. Consequently plastic articulators have not been accepted by the profession or trade.

In addition, dental articulators presently known and available usually mount the dental casts on a manually grooved plaster base carried by the articulator. Since the groove position and size varies, the dental cast is not interchangeable with another articulator. Unless a dentist has made arrangements for obtaining from the dental laboratory the particular dental articulator on which the artificial prosthesis was designed, he is unable to check the accuracy of the finished prosthetic device he received until he has placed it in the patient's mouth.

Because the articulators are constantly sent between the dentist's office and the dental laboratory, they are subject to physical abuses which may render them prematurely unusable.

SUMMARY AND OBJECTS OF INVENTION

The present invention avoids many of the aforementioned problems and deficiencies of the aforementioned prior art devices, and provides a plastic dental articulator having corresponding recessed grid surfaces to which dental casts or models may be secured.

A primary object of the invention is to provide a plastic dental articulator which is simply constructed, light weight, economical to produce and disposable.

Yet another object of the invention is to provide a plastic dental articulator which is rigid, accurate, reliable and easy to use.

Still another object of the invention is to provide a plastic dental articulator which has a gripping surface such as a grid pattern in the articulator itself so that dental casts may be removably mounted and secured directly to the articulator itself. A related object is to provide a plurality of dental articulators each having a grid pattern with the same clearly defined outer boundary so that the outer dimensions of all casts mounted on the articulators are uniform.

A further object is to mount the dental casts within outer peripheral protective walls on an articulator.

Still another object of the invention is to provide a plastic articulator which is graduated around its periphery to aid the laboratory technician and dentist in the analysis and discussion of the dental prosthesis, and to aid in the design and construction of the prosthesis.

A further object is to provide a guide pin for adjustably controlling the spacing between the upper and lower casts.

Yet another object of the invention is to provide a plastic dental articulator which is easily assembled or disassembled and which permits relative lateral excursion movement between the upper and lower members.

Other objects and advantages of the invention will appear from the following description taken in conjunction with the accompanying drawings.

BRIEF DESCRIPTION OF THE DRAWINGS

FIG. 1 is a perspective view of a presently preferred embodiment of the three elements of apparatus in assembled position;

FIG. 2 is a cross-sectional view taken along line 2—2 of FIG. 1, and showing exemplary dental casts mounted thereon;

FIG. 3 is an enlarged fragmentary cross-sectional view taken along line 3—3 in FIG. 2 showing the guide pin in locked position with the upper cup member;

DESCRIPTION OF THE PREFERRED EMBODIMENT

Figure 4:
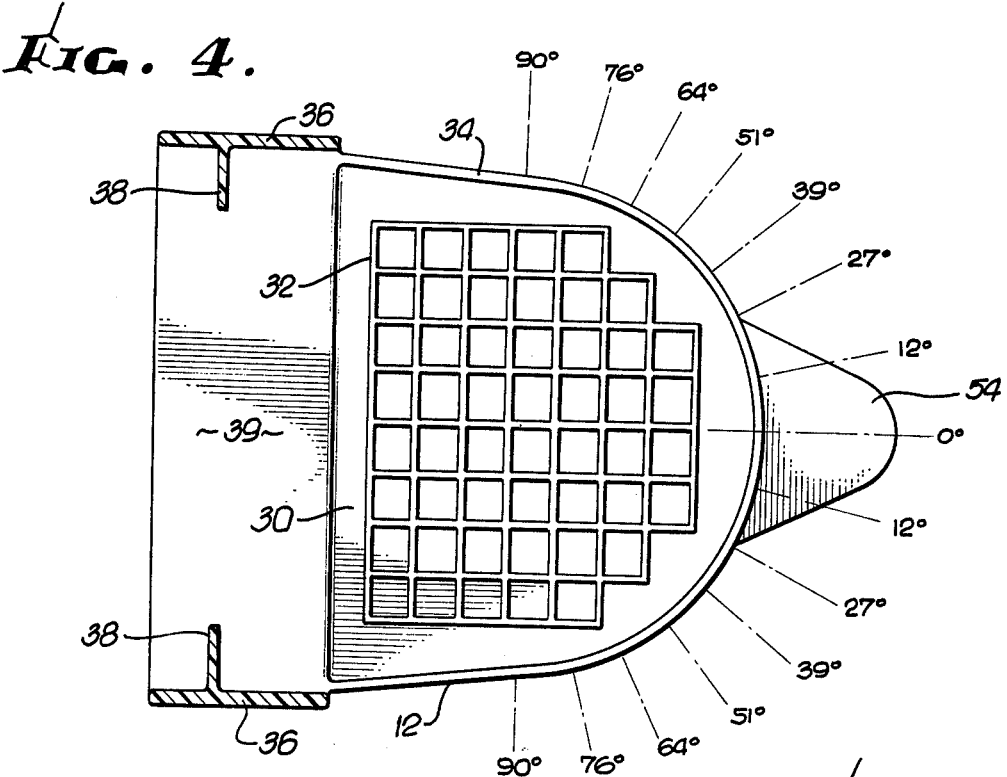
FIG. 4 is a cross-sectional view of the lower cup member taken along line 4—4 of FIG. 2.
Figure 5:
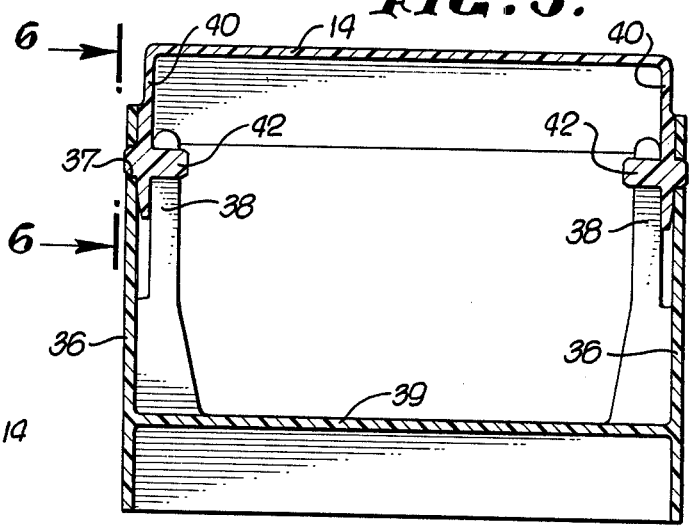
FIG. 5 is a vertical cross-sectional view taken along line 5—5 of FIG. 2 showing the interconnection between the top and bottom cup members.

While the present invention is susceptible to modifications and alternative constructions, an illustrative embodiment is shown in the drawings and will be described in detail hereinbelow. It should be understood, however, that it is not the intention to limit the invention to the particular form disclosed, but, on the contrary, the invention is to cover all modifications, equivalences and alternative constructions falling within the spirit and scope of the invention as expressed in the appended claims.

Referring initially to FIG. 1, there is illustrated a dental articulator 10 having a bottom cup member 12 and a matching top cup member 14, each of which is preferably a unitary element made of plastic such as high-impact styrene. The two cups are pivotally connected at their rearward ends and are spaced apart by an incisal guide pin 16 located at their forward ends.

More specifically, the top cup 14 has a peripheral vertical wall which forms a circumferential lip 24 surrounding a recessed mounting surface 26 having a series of ribs 28 forming a grid projecting therefrom. The invention is not limited to the specific grid pattern shown, but includes any equivalent means for mounting the casts directly on the articulator. A plaster mounting 20 carries a maxillary model or cast 22 corresponding to the patient's upper dental arch. The entire composite cast 20, 22 is preferably enclosed and protected within the circumferential lip 24 which also adds rigidity to the structure and enables the base of all castings to have uniform outer dimensions.

The bottom cup 12 has a corresponding matching recessed surface 30 with a similar mounting grid formed by a grid 32 projecting from the recessed surface 30 and surrounded by a circumferential lip 36. A plaster mounting 20a carrying a mandibular model or cast 22a corresponding to a patient's lower dental arch is also mountable in the same manner as on the upper cup.

At the rearward portion of the lower cup 12 there are a pair of upwardly projecting rami 36, each having a slotted opening 37 therethrough. Flexible fingers 38 adjoin a plate 39 and project upwardly past the opening 37. Each finger is also integral with the bottom end of the rami thereby adding stability to the base of the fingers while leaving their upper ends free and flexible in the forward and rearward direction. This also leaves the upper ends of the rami free and flexible in the lateral direction.

The upper cup 14 has a pair of downwardly projecting side flanges 40 which are spaced apart to fit between the inner surfaces of the rami when the latter are spread apart. Each flange has a dowel 42 extending both inwardly and outwardly of the flanges 40. The outward extension of each dowel projects through the opening 37 in the rami 36, while the inner projection of the dowel abuts the upper portion of the finger 38. Of course, the invention is not limited to these specific mounting details, so long as only manual flexing is required to pivotally connect or disconnect the two cups.

Referring now to FIGS. 1 and 2, there is illustrated a notch 56 on each ramus midway between the recessed surfaces 30 and 26 of the bottom and top members 12 and 14, respectively. The incisal guide pin also has a notch 58 located midway between the recessed surfaces. These three notches define a place midway between the recessed surfaces and provide a reference to be used in the analysis work on the dental casts.

Figure 6:
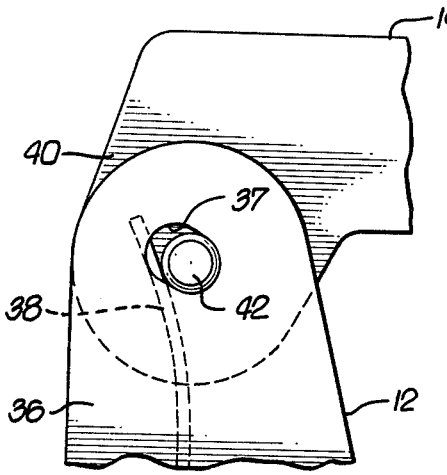
FIG. 6 is an enlarged fragmentary view taken along line 6—6 of FIG. 5.

FIG. 6 best shows the details of the pivotal attachment between the two cup members. The upstanding fingers bias the dowel either forwardly or rearwardly in the slotted opening 37 while being sufficiently flexible to permit relative transverse movement (lateral excursion) between the two cup members to more nearly simulate the movement of the patient's jaws. In the illustrated form, the finger 38 presses the dowel 42 from the rear so it is normally held against the forward and lower end of the slotted opening 37 by the spring force of the finger 38 and its frictional contact with the dowel 42.

The lower cup 12 has a forwardly projecting platform 54 for stopping the bottom end of the guide pin 16. The upper cup 14 has a forwardly projecting apex 50 with a non-circular opening 52 for receiving the guide pin therethrough. By turning a handle 48 at the upper end of the guide pin, the pin can slide in aligned position through the opening, and alternatively can be frictionally jammed in the opening by turning the handle. The desired vertical dimension can be determined by the calibration on the exterior of the guide pin. The outer surfaces of the lips 24 and 34 are also referenced and calibrated with respect to the centerline of the apparatus, in order to aid the technician in constructing and analyzing the plaster dental models or casts and prosthetic devices being constructed thereon. An area 60 is provided on the upper surface of the top cup 14 for the recordation of dental data and the like.

It will therefore be appreciated by those skilled in the art that the exemplary embodiment shown and described employs unique and improved structural features and relationships to simulate the basic anatomical movements and relationships of the mandible and maxilla. It enables the placement of the models or casts of a dental patient's upper and lower dental arch in their proper relative position, thus facilitating the fabrication of a prosthetic device or appliance in anatomical relation to structures within the mouth.

The low cost of production of the exemplary unit described and shown eliminates the need for re-use and makes disposability economically feasible. This feature eliminates the need for inventory control and makes it economically possible for the dental laboratory to return in-process or completed prosthesis to the dentist on the articulator. The dentist will have the opportunity to check out the completed appliance on the casts prior to a patient's visit and retain the articulated casts for utilization during future alterations or repairs.

The relatively light weight of the material facilitates transportation between the dental laboratory and the dentist's office and reduces mailing costs. The material itself can be flushed in boiling water, thus enabling cleaning of the casts without the removal from the articulator.

The use of the shallow dishes or cups provides for uniformity and a neat, clean articulation while saving articulation labor time normally expended to shape, grind and finish the plaster edges. The walls of the cups provide boundaries for the waffle-like grid which engages and holds the casts initially or upon replacement should removal become necessary during fabrication of the prosthesis.

The tripod effect created by the guide pin and the rear portion of the unit provides the necessary rigidity missing from other plastic and many simple metal articulators. The guide pin can easily be locked into position to act as a stop for the closing articulator, thus permitting return to an exact position while avoiding possible impact damage to the casts. In this regard, the incisal guide pin incorporates a unique semicircular cross-sectional shape which enables it to be locked or wedged into fixed position with a slight manual twist. The calibration in millimeters permits it to be set to a given point.

Since the articulator is disposable, patient information can be permanently affixed to the aforementioned space on the top of the upper cup. This helps avoid the possibility of case mixup which may otherwise occur in the dental laboratory or office, and retains necessary information for future or subsequent procedures.

The calibration around the edge of the cups enables transfer of information directly from the written prescription to the working area. By placing a rubber band in the aforementioned notches in the device, a plane is defined midway between the upper and lower surfaces. This provides a guide to the technician who previously used judgment alone in approximating this plane during the articulation of casts and other related functions.

The upper and lower halves of the unit and the incisal guide pin are produced and shipped to the laboratory as three separate sections, thereby requiring minimal shipping and storage space. As previously described, assembly is easily accomplished to join the upper and lower members together at the condular point of rotation. In this regard, the plastic clips or fingers are preferably molded directly with and part of the lower cup member.

Since the upper and lower halves are easily separable even when carrying the plaster mounting base and casts, it is possible to interchange a series of casts, thus facilitating certain common laboratory techniques such as functionally generated path procedures.

Uniformity and ease of separation also make possible the restructuring of certain basic equipment within the laboratory so as to accept the articulator dimensions, thereby eliminating the need to remove the casts from the articulator during certain phases of prosthesis production such as duplication, survey and design. Where removal is necessary, remounting in its original position on the articulator cup is easily accomplished with the grid.

Since plaster and casts are contained within the overall outer dimensions of the articulator, they are protected from damage during shipping and handling.

The aforementioned apparatus and method therefore provides for optimum conditions for work and analysis on the casts or models in either initial or remounted position on the cup members, with the choice of either separating the cups for independent work or pivotally joining them together in cooperative relationship.

We claim as our invention:

1. A device for dental articulation comprising in combination:
   an upper cup member having first peripheral wall means for receiving a plaster mounted cast therebetween;
   a lower cup member having second peripheral wall means for receiving another plaster mounted cast therebetween;
   pivotal means connected to each of said cup members for allowing manually induced relative movement between said cup members, said pivotal means comprising a pair of horizontal dowels on one of said cup members respectively engagable with and rotatable in a pair of bearings on the outer of said cup members and wherein said bearings are slotted to enable relative lateral movement between said cup members.

2. The device of claim 1 including biasing means coupled to said pivotal means for normally holding said dowels in one end of said slotted bearings.

3. A device for dental articulation including in combination:
   an upper cup member having first peripheral wall means for receiving a plaster mounted cast therebetween;
   a lower cup member having second peripheral wall means for receiving another plaster mounted cast therebetween;
   pivotal means connected to each of said cup members for allowing manually induced relative movement between said cup members, wherein said pivotal means comprises a pair of legs extending upwardly on said bottom cup member and being laterally flexible at their upper ends for pivotally engaging said top cup member; and
   a vertical displacement pin opposite said pivotal means and extending between said cup member, with marked means on said pin and said legs for defining a reference plane between said cup members.

* * * * *